(12) United States Patent  (10) Patent No.: US 8,348,963 B2
Wilson  (45) Date of Patent: Jan. 8, 2013

(54) LEAFLET REINFORCEMENT FOR REGURGITANT VALVES

(75) Inventor: Robert F. Wilson, Roseville, MN (US)

(73) Assignee: HLT, Inc., Maple Grove, MN (US)

( * ) Notice: Subject to any disclaimer, the term of this patent is extended or adjusted under 35 U.S.C. 154(b) by 796 days.

(21) Appl. No.: 10/613,121

(22) Filed: Jul. 3, 2003

(65) Prior Publication Data

US 2004/0106989 A1    Jun. 3, 2004

Related U.S. Application Data

(60) Provisional application No. 60/393,794, filed on Jul. 3, 2002.

(51) Int. Cl.
*A61B 17/08* (2006.01)
(52) U.S. Cl. .......................... 606/151; 606/213
(58) Field of Classification Search .................. 606/151, 606/898, 213, 41; 128/898
See application file for complete search history.

(56) References Cited

U.S. PATENT DOCUMENTS

| 15,192 | A | 6/1856 | Peale |
| 5,046,497 | A | 9/1991 | Millar |
| 5,071,407 | A | 12/1991 | Termin et al. |
| 5,221,261 | A | 6/1993 | Termin et al. |
| 5,258,023 | A | 11/1993 | Reger |
| 5,326,372 | A | 7/1994 | Mhatre et al. |
| 5,397,351 | A | 3/1995 | Pavcnik et al. |
| 5,409,019 | A | 4/1995 | Wilk |
| 5,411,552 | A | 5/1995 | Andersen et al. |
| 5,429,144 | A | 7/1995 | Wilk |
| 5,496,329 | A | 3/1996 | Reisinger |
| 5,725,552 | A | 3/1998 | Kotula et al. |
| 5,840,081 | A | 11/1998 | Andersen et al. |
| 5,846,261 | A | 12/1998 | Kotula et al. |
| 5,855,614 | A | 1/1999 | Stevens et al. |
| 5,924,424 | A | 7/1999 | Stevens et al. |
| 5,944,738 | A | 8/1999 | Amplatz et al. |
| 5,957,949 | A | 9/1999 | Leonhardt et al. |
| 5,972,017 | A | 10/1999 | Berg et al. |
| 6,036,702 | A | 3/2000 | Bachinski et al. |
| 6,074,416 | A | 6/2000 | Berg et al. |
| 6,074,418 | A | 6/2000 | Buchanan et al. |
| 6,083,219 | A | * 7/2000 | Laufer .................. 606/27 |
| 6,106,497 | A | 8/2000 | Wang |
| 6,113,612 | A | 9/2000 | Swanson et al. |
| 6,120,432 | A | 9/2000 | Sullivan et al. |
| 6,123,715 | A | 9/2000 | Amplatz |
| 6,149,681 | A | 11/2000 | Houser et al. |
| 6,165,183 | A | 12/2000 | Kuehn et al. |

(Continued)

FOREIGN PATENT DOCUMENTS

FR    0014992    11/2000

(Continued)

*Primary Examiner* — Gary Jackson
*Assistant Examiner* — Diane Yabut
(74) *Attorney, Agent, or Firm* — Inskeep IP Group, Inc.

(57) ABSTRACT

A support, and a method for attaching said support, for providing additional strength to existing regurgitant or prolapsed valve leaflets. The support restores an otherwise non-functioning, or poorly functioning, native valve to a functioning condition, obviating the need for a complete valve removal or replacement. The support may also be applied to a functioning valve leaflet as a prophylactic measure against future failure. The delivery method includes a delivery mechanism for attaching the support to the native valve leaflet.

12 Claims, 9 Drawing Sheets

U.S. PATENT DOCUMENTS

| | | | |
|---|---|---|---|
| 6,165,215 A | 12/2000 | Rottenberg et al. | |
| 6,168,614 B1 | 1/2001 | Andersen et al. | |
| 6,200,336 B1 | 3/2001 | Pavcnik et al. | |
| 6,287,334 B1 | 9/2001 | Moll et al. | |
| 6,293,955 B1 | 9/2001 | Houser et al. | |
| 6,334,873 B1 | 1/2002 | Lane et al. | |
| 6,336,937 B1 | 1/2002 | Vonesh et al. | |
| 6,338,740 B1 | 1/2002 | Carpentier | |
| 6,358,277 B1 | 3/2002 | Duran | |
| 6,358,279 B1 | 3/2002 | Tahi et al. | |
| 6,419,681 B1 | 7/2002 | Vargas et al. | |
| 6,423,090 B1 | 7/2002 | Hancock | |
| 6,425,916 B1 | 7/2002 | Garrison et al. | |
| 6,440,163 B1 | 8/2002 | Swanson et al. | |
| 6,440,164 B1 | 8/2002 | DiMatteo et al. | |
| 6,454,798 B1 | 9/2002 | Moe | |
| 6,454,799 B1 | 9/2002 | Schreck | |
| 6,458,153 B1 | 10/2002 | Bailey et al. | |
| 6,475,239 B1 | 11/2002 | Campbell et al. | |
| 6,494,889 B1 | 12/2002 | Fleischman et al. | |
| 6,494,909 B2 | 12/2002 | Greenhalgh | |
| 6,503,272 B2 | 1/2003 | Duerig et al. | |
| 6,508,833 B2 | 1/2003 | Pavcnik et al. | |
| 6,511,491 B2 | 1/2003 | Grudem et al. | |
| 6,752,813 B2 * | 6/2004 | Goldfarb et al. | 606/139 |
| 2001/0007956 A1 | 7/2001 | Letac et al. | |
| 2001/0010017 A1 | 7/2001 | Letac et al. | |
| 2001/0039450 A1 | 11/2001 | Pavcnik et al. | |
| 2002/0055772 A1 | 5/2002 | McGuckin, Jr. et al. | |
| 2002/0173841 A1 * | 11/2002 | Ortiz et al. | 623/2.11 |
| 2002/0198594 A1 | 12/2002 | Schreck | |
| 2003/0014104 A1 | 1/2003 | Cribier | |
| 2003/0023300 A1 | 1/2003 | Bailey et al. | |
| 2003/0023303 A1 | 1/2003 | Palmaz et al. | |

FOREIGN PATENT DOCUMENTS

| | | |
|---|---|---|
| WO | WO 00/15149 | 3/2000 |
| WO | WO 02/24119 | 3/2002 |

* cited by examiner

Fig. 1a
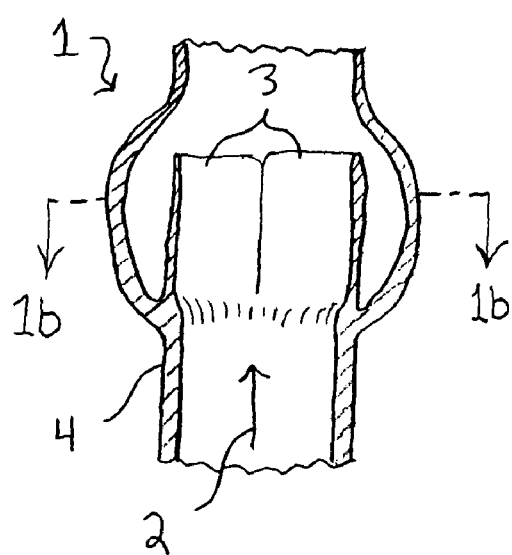
Fig. 2a
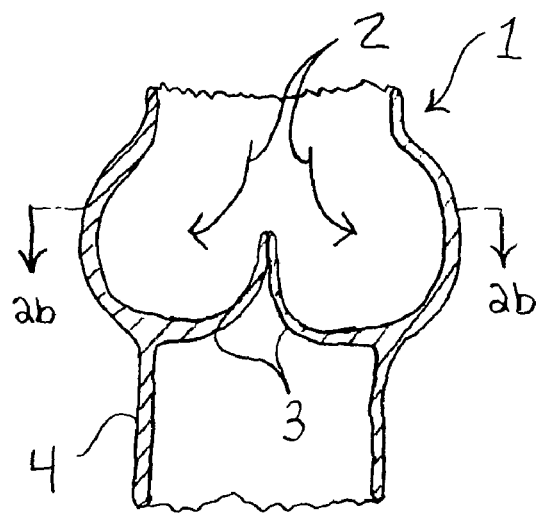
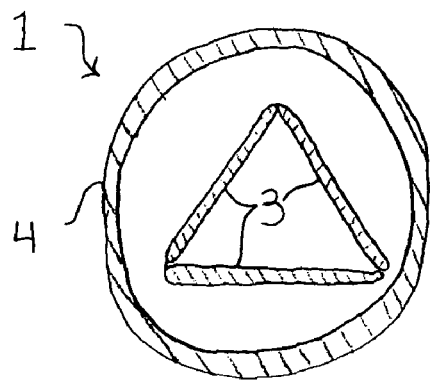
Fig. 1b
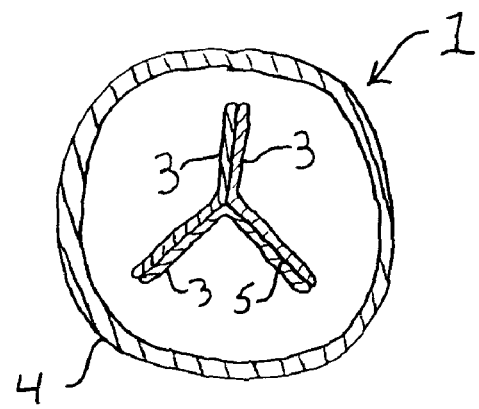
Fig. 2b

Fig. 3a
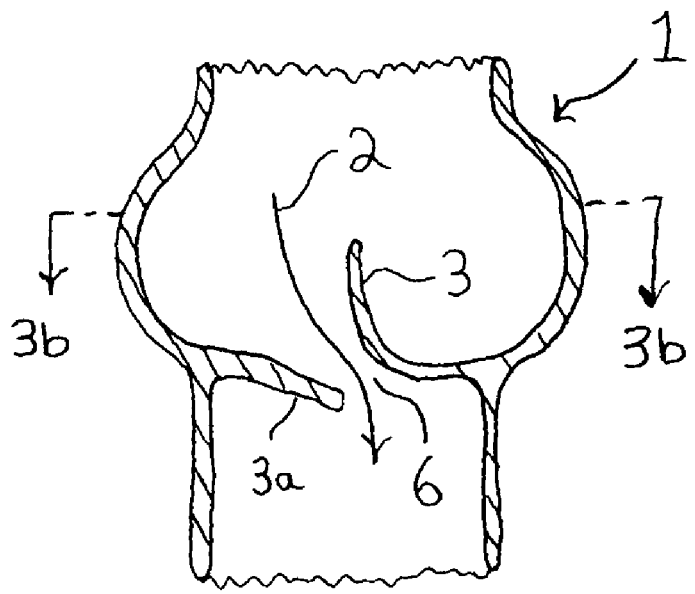
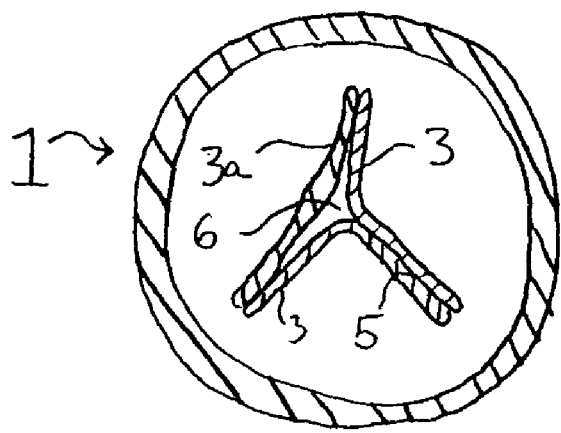
Fig. 3b

LEAFLET REINFORCEMENT FOR REGURGITANT VALVES

CROSS-REFERENCE TO RELATED APPLICATION

This application claims the benefit of U.S. Provisional Application No. 60/393,794, filed Jul. 3, 2002, the contents of which are incorporated by reference.

BACKGROUND OF THE INVENTION

Blood vessel valves include flexible tissue leaflets that passively alternate between open and closed positions as the forces of a blood stream act upon them. As blood flows in a first direction, the leaflets are urged apart from each other, and allow the blood to pass. Between pulses, as the blood attempts to flow in a reverse direction, the blood acts upon upstream surfaces of the individual leaflets, causing the leaflets to move inwardly. As the leaflets move inwardly, the edges of the individual leaflets (two, in the case of bicuspid valves, and three in the case of tricuspid valves) abut against each other, effectively blocking the blood flow in the reverse direction.

If the individual leaflets suffer degradation in structural integrity, such as degeneration, a prolapse condition may result. FIGS. 1 through 3 demonstrate the mechanics of a regurgitant valve with leaflet prolapse. FIGS. 1a and 1b show a healthy tricuspid valve 1 in the open position. The direction of blood flow is indicated by arrow 2. The valve 1 includes three leaflets 3 growing into the lumen of a blood vessel 4. It can be seen that when the blood is flowing in the direction shown by arrow 2 of FIG. 1a, the flexible valve leaflets 3 naturally fold themselves against the interior walls of the blood vessel 4, thereby minimizing their impact on blood flow in that direction.

As depicted in FIG. 2a, when blood attempts to flow in the reverse direction, between cardiac pulses, these valve leaflets 3 move inward, toward each other. As best shown in FIG. 2b, when the leaflets 3 abut, they form a seal 5, effectively preventing fluid flow in the direction of arrows 2 from FIG. 2a. The seal 5 can only be formed if all three valve leaflets 3 are structurally sound.

When a valve, such as valve 1 of FIG. 3, has a prolapsed leaflet 3a, the seal 5 cannot be effectively formed. Leaflet 3a lacks the structural integrity of the healthy leaflets 3. When the flow is reversed, as indicated by arrow 2, the healthy leaflets 3 balloon inwardly. However, the prolapsed leaflet 3a falls away from the seal 5, leaving a significant gap 6 in the seal 5. Blood passes through the gap 6, resulting in a loss of systolic pressure, as well as a reduction in the pumping efficacy of the heart.

Current methods of repairing prolapsed valves involve replacing the valve entirely with a prosthetic valve. The structurally sound leaflets are not preserved. It would be advantageous to provide a method of repairing a prolapsed valve, leaving as much of the native valve as possible intact, thereby minimizing the risk of rejection, and preserving the healthy leaflets. Percutaneous treatment would obviate the risks associated with open heart surgery.

SUMMARY OF THE INVENTION

In one aspect of the present invention, there is a method for repairing a prolapsed valve that involves reinforcing the prolapsed leaflet or leaflets to reestablish the structural integrity thereof. The method involves attaching a support to one or both sides of the valve. The support is constructed and arranged to allow the leaflet to open when blood is flowing through the valve in the natural direction. When the flow is reversed during a diastole, the support resists, preventing the leaflet from prolapsing.

In another aspect of the present invention, a support is provided that is attachable to the downstream side of a prolapsed valve leaflet. The support includes an attachment mechanism, preferably barbs, staples, or similar suitable tissue-grabbing means. The support may be bifurcated with one or more hinge, allowing one side of the support to pivot relative to the second side. The hinge is constructed and arranged with a stop, so that the hinge prevents pivoting past a sealing point. Preferably, the hinge is constructed to avoid pinching the leaflet tissue with the stop is reached.

Another aspect of the present invention provides a support that is attachable to the upstream side of a prolapsed valve leaflet. The construction of the upstream support is very similar to that of the downstream support. The upstream support also includes an attachment mechanism, preferably barbs, staples, or similar suitable tissue-grabbing means. Again, the support may be bifurcated with one or more hinge, allowing one side of the support to pivot relative to the other side. The hinge is also constructed and arranged with a stop, so that the hinge prevents pivoting past a sealing point. Placing the support on the upstream side of the valve may be advantageous because the stress encountered during diastole, when the support is preventing the leaflet from prolapsing due to the pressure of the blood, acts in conjunction with the attachment mechanism, rather than against it. Thus, the support is less likely to become separated from the leaflet.

Yet another aspect of the present invention provides a support that includes both upstream and downstream members. These members are similar in construction to the upstream and downstream members. However, the attachment mechanism used in this aspect takes advantage of the additional structure provided by the opposing support. The opposing supports lock together, through the prolapsed leaflet, sandwiching the leaflet therebetween. Preferably, one member includes male connectors, while the other member includes corresponding female connectors. Alternatively, each side includes one or more male and one or more female connectors, and the other member includes corresponding mating connectors. Whereas the downstream member may provide a single hinge, the upstream member may provide a double or triple hinge, constructed and arranged to allow the upstream member to move with the downstream member, without changing the relative position between the two members. Providing such an arrangement avoids the occurrence of locked hinges and/or tearing the leaflet tissue between the two members. Alternatively, one or both supports may be hingeless.

Still another aspect of the present invention provides a support with a more complex, multi-member structure, flexible in one direction but rigid in another direction. This structure obviates the necessity of hinges. The support members form a frame with either an open or covered interior.

A further aspect of the present invention includes a woven, pressed, laminar or similar substrate-like hingeless support. This support operates on the principle that strength is achieved in an otherwise flimsy substrate when the substrate is curved. This principle is easily demonstrated by holding a piece of paper while imparting a curve onto the paper with one's fingers. The paper can be made to easily support itself or even to hold other objects on the concave side, without supporting opposite sides of the paper. However, placing pressure on the convex side of the curved paper causes the paper to quickly bend. Steel tape measures operate on this principle.

The tape measures are curved and can be bent easily in one direction but are relatively rigid in the opposite direction.

Yet another aspect of the present invention includes a method of attaching a support to a prolapsed valve leaflet. The method involves passing a wire from the aorta through the prolapsed valve. A catheter is then guided over the wire that contains the support mechanism. Preferably, the support mechanism includes a biasing means that allows the support to be pre-loaded in the catheter such that, when released from the catheter sheath, the support mechanism attaches itself to the prolapsed valve leaflet. Alternatively, a positioning means is provided so the support members do not require pre-loading in the catheter unit. The positioning means would allow manual manipulation of the support members during placement. The support is preferably removably attached to the leaflet, thereby allowing removal and reattachment if necessary.

BRIEF DESCRIPTION OF THE DRAWINGS

FIG. 1a is a sectional view of a healthy native tricuspid valve in an open position;

FIG. 1b is a sectional view of the valve of FIG. 1a taken along lines 1b-1b;

FIG. 2a is a sectional view of a healthy tricuspid valve in a closed position;

FIG. 2b is a sectional view of the valve of FIG. 2a taken along lines 2b-2b;

FIG. 3a is a sectional view of a native prolapsed valve;

FIG. 3b is a sectional view of the valve of FIG. 3a taken along lines 3b-3b;

DETAILED DESCRIPTION OF THE INVENTION

Figure 4:
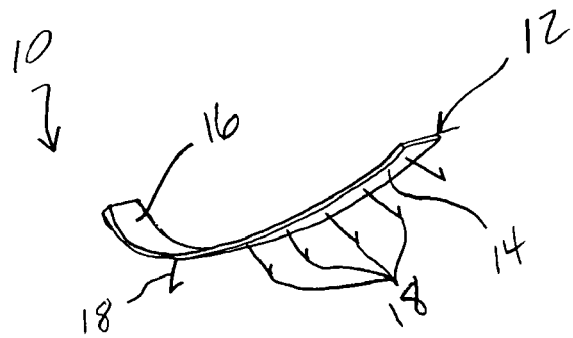
FIG. 4 is a perspective view of an unhinged downstream embodiment of the present invention.

Referring now to the Figures, and first to FIG. 4, there is shown unhinged embodiment of a support 10 of the present invention. Support 10 includes a support member 12, which is curved to approximately match the curve of a healthy valve leaflet in a closed position. The curve defines a convex side 14 and a concave side 16 of the support member 12. A plurality of barbs 18 extend from the support member 12, and are constructed and arranged to penetrate and catch the tissue of a prolapsed leaflet, securing the support member 12 thereto. That the barbs 18 extend from the convex side indicates that the support 10 of FIG. 4 is constructed and arranged for attachment to the downstream side of a prolapsed leaflet.

The support 10 is a biocompatible material. Acceptable biocompatible metals that could be used to construct the support 10 include, but are not limited to, Nitonol, stainless steel, titanium, and other appropriate metals. Acceptable nonmetal biocompatible materials include, but are not limited to, PTFE, pyrolytic carbon, or any appropriate polymer.

Figure 5:
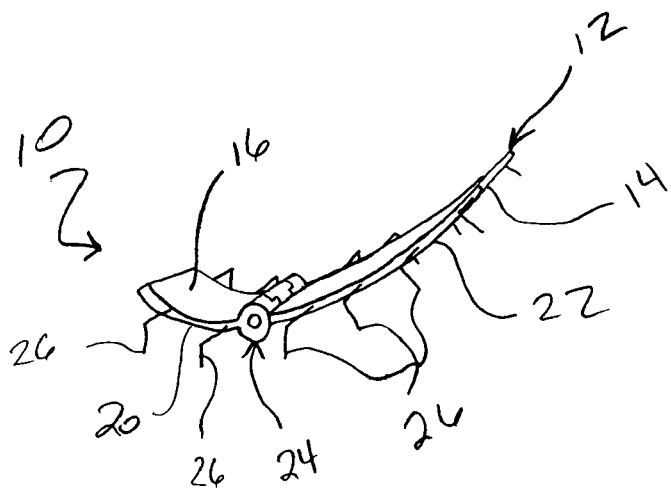
FIG. 5 is a perspective view of a hinged downstream embodiment of the present invention.
Figure 6:
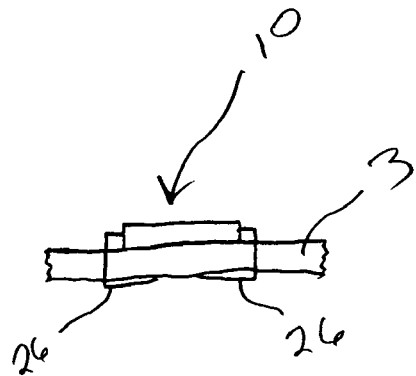
FIG. 6 is an end view of the embodiment of FIG. 5 attached to a valve leaflet.

FIG. 5 shows a hinged embodiment of a support 10. The support 10 is bifurcated into a first part 20 and a second part 22. The first part 20 and the second part 22 are connected with a hinge 24, which allows the second part 22 to rotate relative to the first part 20. Rather than the barbs 18 shown in FIG. 4, the support 10 of FIG. 5 uses a plurality of staples 26 as an attachment mechanism. FIG. 6 shows the staples 26 attaching the support 10 to a valve leaflet 3. The staples 26 are shown with a hinged embodiment 10 but there is no association between the staples 26 and the hinge 24. The barbs 18 of FIG. 4 could be used with a hinged embodiment of support 10, and vice versa.

Figure 7:
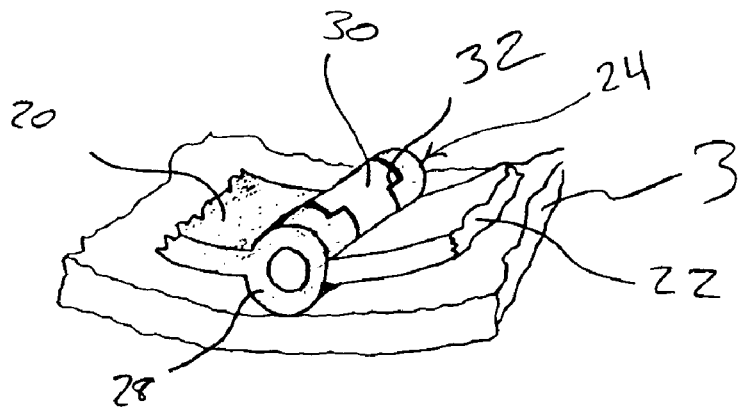
FIG. 7 is a perspective view of a downstream hinge of the present invention.

The hinge 24 is preferably designed to prevent pinching the valve leaflet 3 during operation. FIG. 7 provides a detailed view of the hinge 24. It can be seen that the hinge 24 includes a first part component 28, integral with the first part 20 and a second part component 30 integral with the second part 22. The components 28 and 30 are constructed and arranged to form an interfering stop 32 on a side opposite of the valve leaflet 3.

Figure 8:
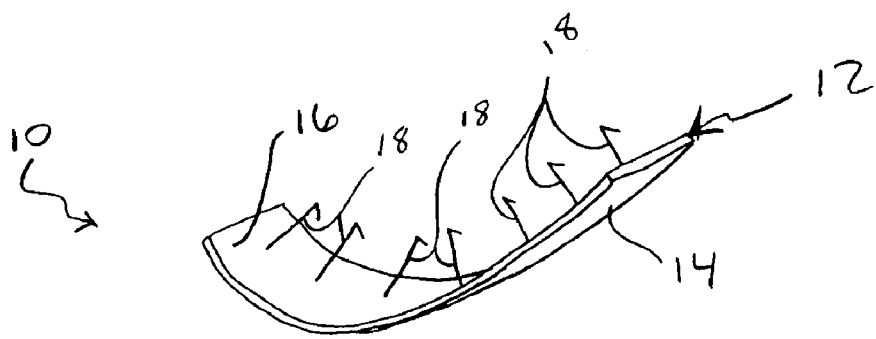
FIG. 8 is a perspective view of an unhinged upstream embodiment of the present invention.

FIG. 8 shows a support 10 constructed and arranged for attachment to an upstream side of a valve leaflet. Again, the support member 12 has a convex side 14 and a concave side 16. However, the attachment mechanism, shown as barbs 18, protrude from the concave side 16, placing the support member 12 on the upstream, convex side of the leaflet.

Figure 9:
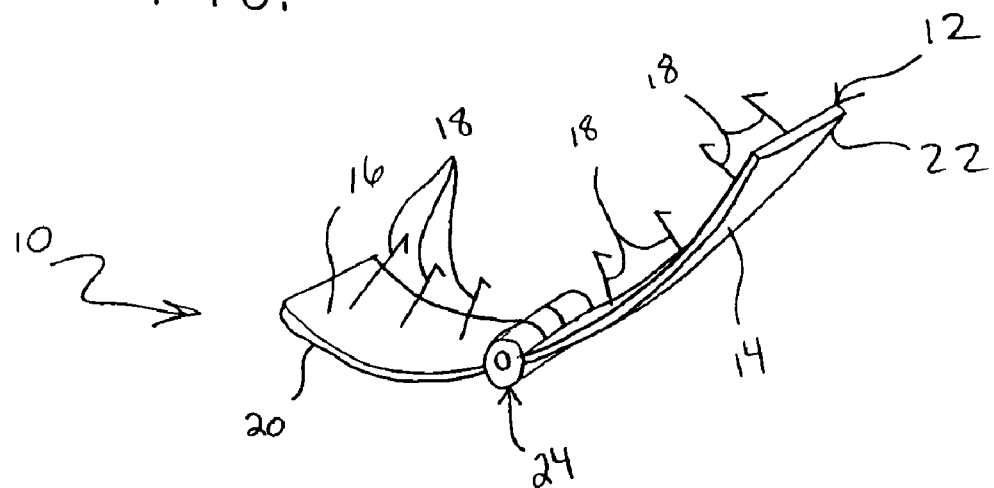
FIG. 9 is a perspective view of a hinged upstream embodiment of the present invention.

FIG. 9 shows a hinged support 10 constructed and arranged for attachment to an upstream side of a valve leaflet. Again, the attachment mechanism, a plurality of barbs 18, protrudes from the concave side 16. The hinge 24 of the upstream, hinged embodiment includes a stop on the upstream side, so as to prevent pinching the leaflet tissue.

Figure 10:
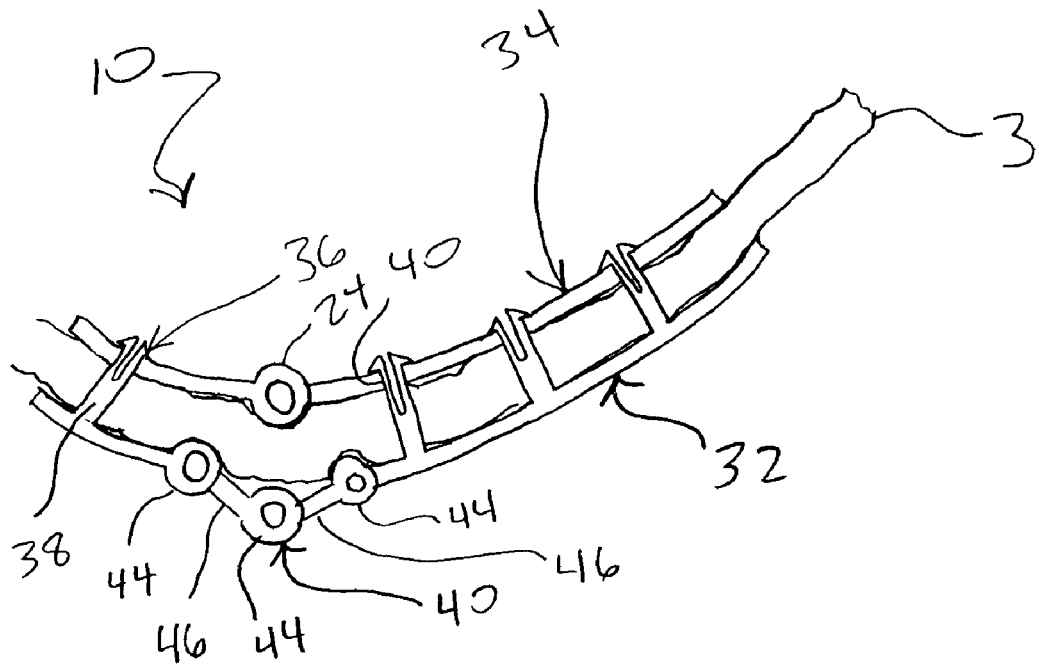
FIG. 10 is a side elevation of a hinged embodiment of the present invention having members on both the upstream and downstream sides of a prolapsed leaflet.

FIG. 10 shows a support 10 that provides additional support and is less reliant on the structural integrity of the leaflet tissue for attachment purposes than the aforementioned embodiments. The support 10 includes an upstream member 32 and a downstream member 34. The upstream member 32 is attached to the downstream member 34 through the valve leaflet 3 with an attachment mechanism 36. The attachment mechanism 36 shown includes a plurality of male posts 38 that extend through and engage corresponding apertures 40 through the downstream member 34. A variety of alternatives may be effectively used as attachment mechanism 36. For example, the male posts could extend from the downstream member 34 into the upstream member 32. Each support 32 and 34 could include both posts and apertures for engaging a corresponding pattern in the opposing support. The apertures do not have to extend through to the opposite side of the defining support. Also, one or both supports could employ magnets that cause the two supports 32 and 34 to be attracted to each other across the leaflet tissue 3.

The support 10 of FIG. 10 also includes a hinge assembly 42, however an unhinged two-sided support is also considered within the scope of the present invention. The hinge assembly 42 includes a single hinge 24 on the downstream member 34, which may be similar to the hinge shown in FIG. 7. The upstream member 32 includes two, or preferably three hinges 44 interconnected with connecting members 46. The connecting members 46 add length to the hinge assembly 42 such that, when the support 10 bends to an open position, the upstream and downstream members 32 and 34 do not move relative to each other.

Figure 11:
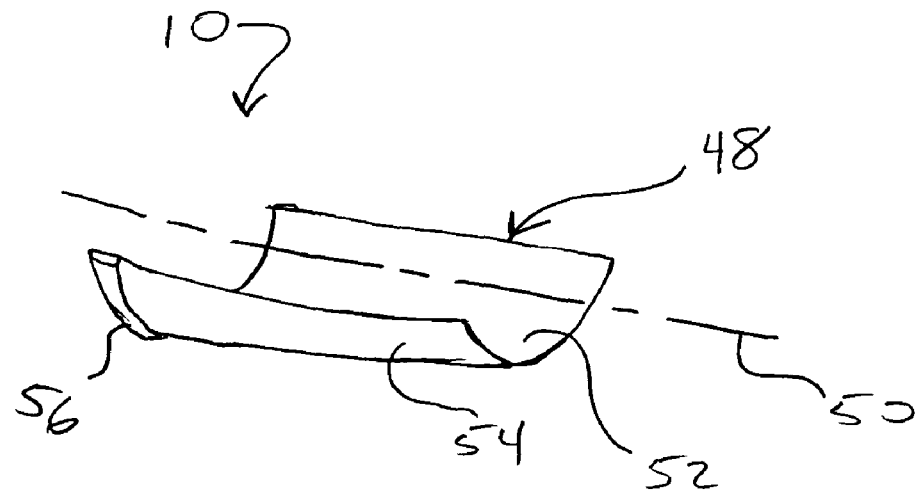
FIG. 11 is a perspective view of a substrate embodiment of the present invention in a closed position.

FIG. 11 shows an alternative design for a support 10 that incorporates a substrate 48. The substrate 48 is preferably a flexible, biocompatible fabric that is at least somewhat resistant to stretching and compressing. The substrate is curved around a longitudinal axis 50 to form a concave side 52 and a convex side 54. The curve is imparted to the substrate 48 using a heat, mechanical, or chemical forming process. Alternatively, or additionally, a curved brace 56 is included at one end of the support 10 that is to be placed near the base of the valve leaflet, proximal the arterial wall.

Figure 12:
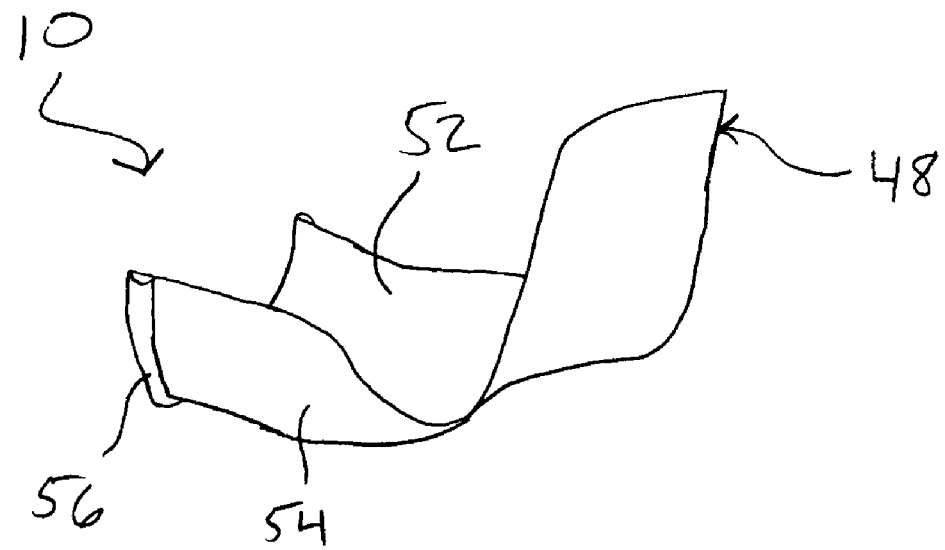
FIG. 12 is a perspective view of a substrate embodiment of the present invention in an open position.

Imparting a curve around the longitudinal axis 50 provides a directional strength to the support 10 that lends itself to the application of supporting a prolapsed valve leaflet. As seen in FIG. 12, when blood flows in a systolic direction, the blood pushes on the convex side 54 of the support 10 and causes the support to buckle, allowing the blood to pass through the valve. The curve does not add significant strength to the support 10 in this direction. However, when the pressure reverses, such as during diastole, the support 10 snaps back into the closed position shown in FIG. 11. Pressure against the concave side 52 is met with the resistance imparted to the support 10 by the curve, preventing the support 10 from buckling toward the convex side 54.

The support 10 of FIGS. 11 and 12 is versatile enough to be placed on either or both sides of a prolapsed valve. Attachment mechanisms such as staples, permanent sutures, adhesives, magnets, or the like could be used to secure the support 10 to the valve leaflet.

Figure 13:
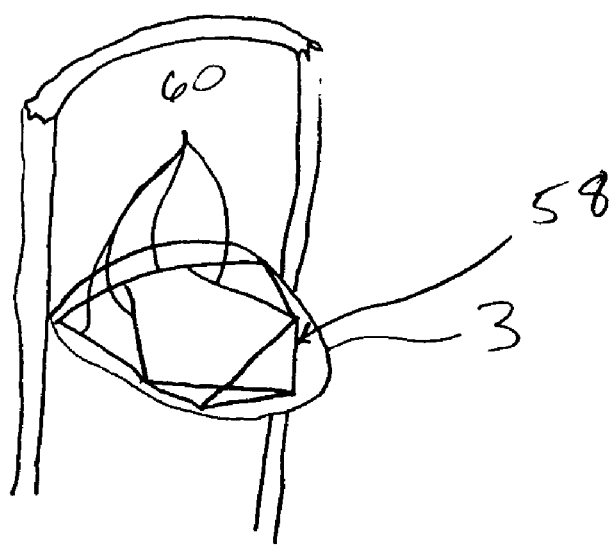
FIG. 13 is a perspective view of a multi-member structure embodiment of the present invention.

FIG. 13 shows another embodiment of a support 10 attached to a prolapsed valve leaflet 3. The support 10 includes a network 58 of interconnected structures 60. The structures 60 are constructed and arranged to allow the support 10 to bend in a downstream direction to an open position, yet provides resistance to bending in an upstream direction during a diastole. The support 10 may include a covering over the network 58 or the network 58 may remain open.

A method of securing a support 10 to a prolapsed valve leaflet 3 is illustrated in FIGS. 14a-d. A guide wire 62 is threaded through a blood vessel 4 to the site where the support 10 is to be installed. A catheter sheath 64, containing the support 10, is then fed along the guide wire 62 until the valve 1 is reached and the support 10 is adjacent the target leaflet 3. The sheath 64 is then carefully retracted until the support 10 is exposed and free to rotate.

Figure 14D:
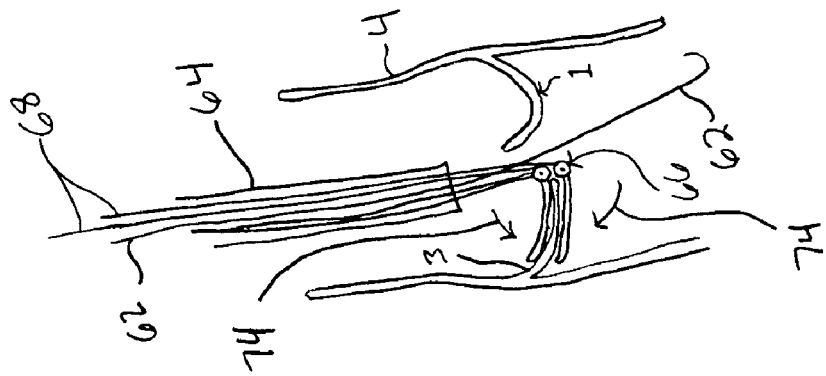
FIGS. 14a-d are a series of drawings depicting a preferred method of attaching a support to a prolapsed leaflet.
Figure 14C:
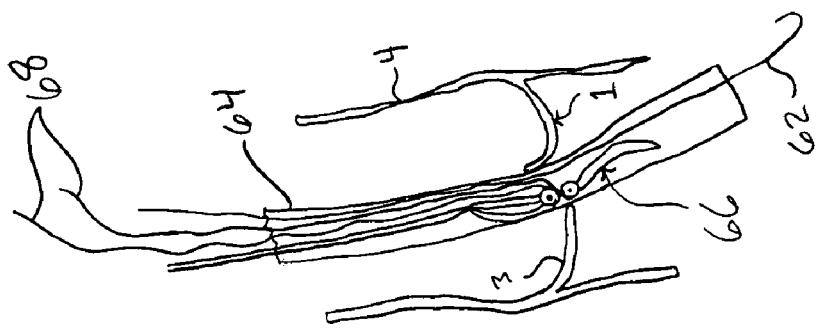
Figure 14B:
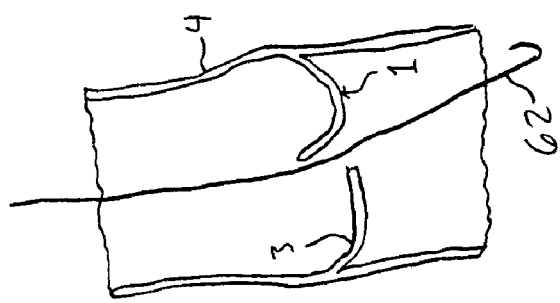
Figure 14A:
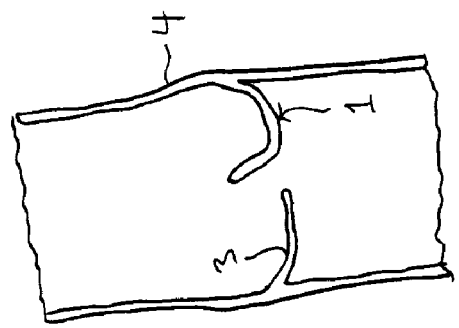
Figure 15:
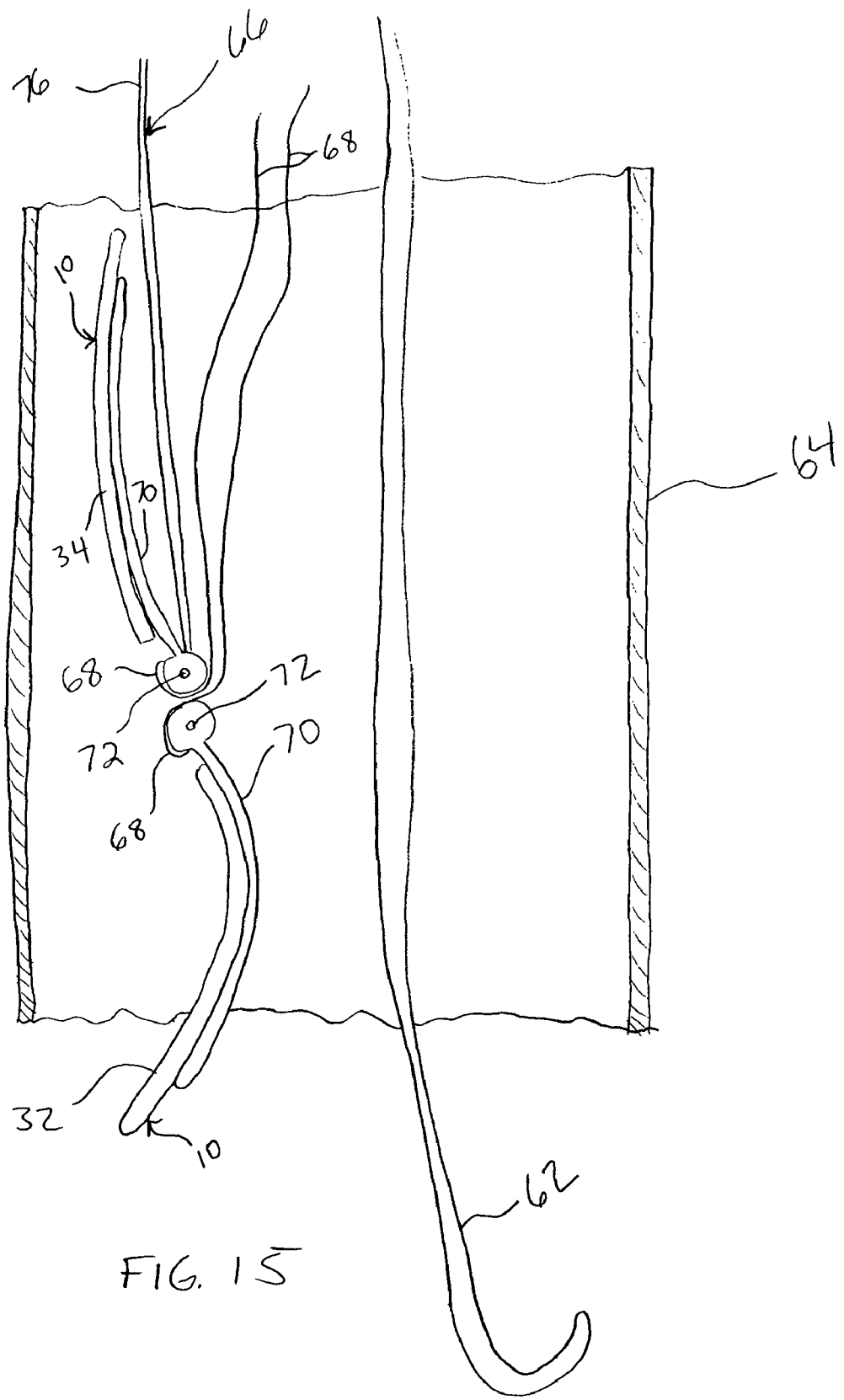
FIG. 15 is an elevation of a preferred delivery device of the present invention; and, FIG. 16 is a perspective view of a preferred delivery device of the present invention.
Figure 16:
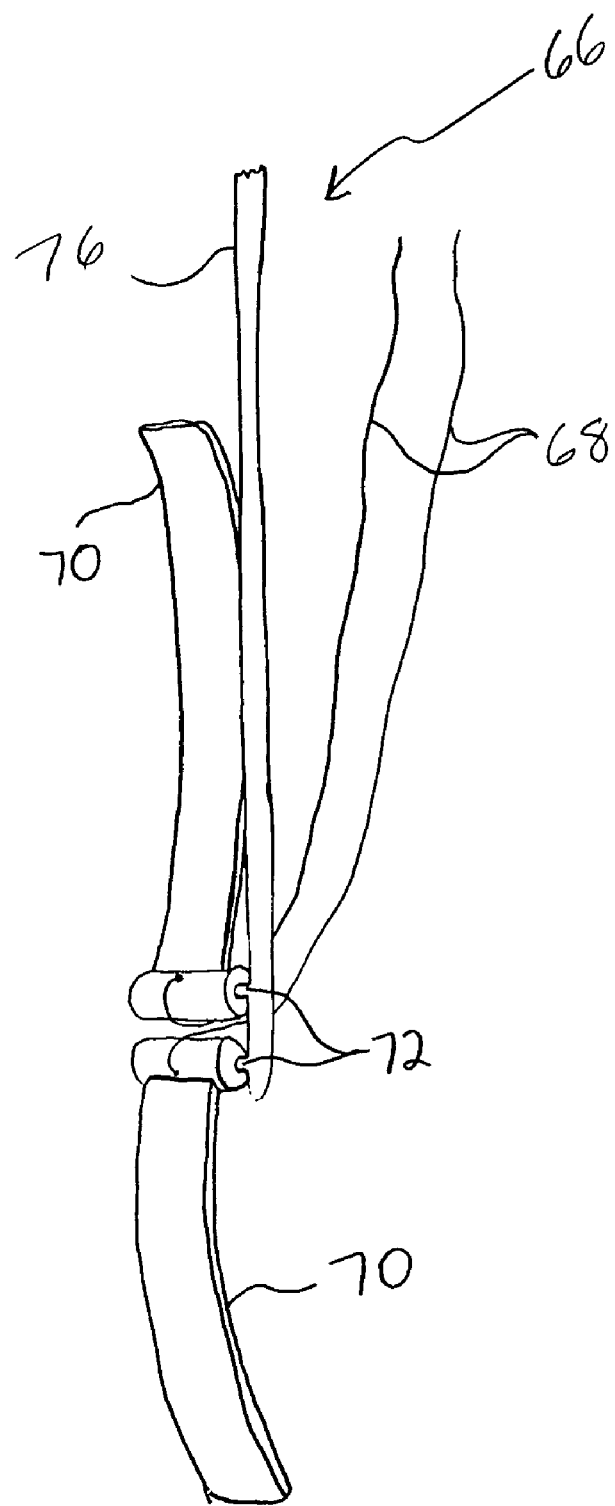

The support 10 is attached at one end to a delivery mechanism 66, best shown in FIGS. 15 and 16. The delivery mechanism 66 is used to rotate the support 10 into place after the sheath 64 is removed. Rotation is achieved by manually pulling on activation strings 68. When the strings 68 are pulled, the delivery arms 70 rotate around axles 72 in the directions shown by arrows 74 (FIG. 14d). The support 10, being temporarily attached to the delivery arms 70, rotate therewith. It may be necessary to hold a carrier 76, on which the arms 70 are pivotally mounted, when pulling the strings 68, in order to maintain the position of the delivery mechanism 66. Once in place, the attachment mechanism of the support penetrates the leaflet, or otherwise fixes the support 10 to the leaflet, and allows the delivery arms 70 to be dislodged from the support 10. The delivery mechanism 66 and guide wire 62 are then retracted into the sheath 64 and the sheath 64 is removed from the patient.

The delivery mechanism 66 is shown in FIG. 15 as delivering a support 10 that includes both an upstream member 32 and a downstream member 34. However, the same delivery mechanism 66, having two delivery arms 70, could also be used to deliver supports having only one support member, either upstream or downstream. The unused arm 70 provides a surface against which the other arm acts to secure the support to the leaflet. The unused arm also provides a surface against which staples, if used as an attachment mechanism, can be folded into an attached arrangement.

The foregoing description addresses embodiments encompassing the principles of the present invention. The embodiments may be changed, modified and/or implemented using various types of arrangements. Those skilled in the art will readily recognize various modifications and changes that may be made to the invention without strictly following the exemplary embodiments and applications illustrated and described herein, and without departing from the scope of the invention, which is set forth in the following claims.

What is claimed is:

1. A method of reinforcing a native valve leaflet comprising implanting a sutureless reinforcing device to the valve leaflet, said support extending radially into said leaflet and positioned away from adjacent native valve leaflets, thereby allowing any free edges of the valve leaflet to form a seal with free edges of the adjacent native valve leaflets during diastole.

2. The method of claim 1 wherein implanting a reinforcing device to the at least one valve leaflet comprises attaching a reinforcing support to a downstream surface of the at least one valve leaflet.

3. The method of claim 1 wherein implanting a reinforcing device to the at least one valve leaflet comprises attaching a reinforcing support to an upstream surface of the at least one valve leaflet.

4. The method of claim 1 wherein implanting a reinforcing device to the at least one valve leaflet comprises attaching a reinforcing support to both an upstream surface and a downstream surface of the at least one valve leaflet.

5. The method of claim 4 wherein attaching a reinforcing support to both an upstream surface and a downstream surface of the at least one valve leaflet comprises sandwiching the at least one valve leaflet between adjacent support members on opposite sides of the at least one valve leaflet.

6. The method of claim 5 wherein sandwiching the at least one valve leaflet between adjacent support members on opposite sides of the at least one valve leaflet comprises sandwiching the at least one valve leaflet between adjacent, interlocking support members on opposite sides of the at least one valve leaflet.

7. A method of reinforcing a native valve comprising implanting at least one sutureless reinforcing device to at least one valve leaflet, each of said at least one sutureless reinforcing devices corresponding to a single leaflet such that no sutureless reinforcing device contacts more than one leaflet, said at least one sutureless reinforcing device positioned away from free edges of said at least one valve leaflet, thereby allowing any free edges of the at least one valve leaflet to form a seal with free edges of adjacent leaflets during diastole.

8. The method of claim 7 wherein implanting at least one reinforcing device to the at least one valve leaflet comprises attaching a reinforcing support to a downstream surface of the at least one valve leaflet.

9. The method of claim 7 wherein implanting at least one reinforcing device to the at least one valve leaflet comprises attaching a reinforcing support to an upstream surface of the at least one valve leaflet.

10. The method of claim 7 wherein implanting at least one reinforcing device to the at least one valve leaflet comprises attaching a reinforcing support to both an upstream surface and a downstream surface of the at least one valve leaflet.

11. The method of claim 10 wherein attaching a reinforcing support to both an upstream surface and a downstream surface of the at least one valve leaflet comprises sandwiching the at least one valve leaflet between adjacent support members on opposite sides of the at least one valve leaflet.

12. The method of claim 11 wherein sandwiching the at least one valve leaflet between adjacent support members on opposite sides of the at least one valve leaflet comprises sandwiching the at least one valve leaflet between adjacent, interlocking support members on opposite sides of the at least one valve leaflet.

* * * * *

UNITED STATES PATENT AND TRADEMARK OFFICE
CERTIFICATE OF CORRECTION

PATENT NO. : 8,348,963 B2
APPLICATION NO. : 10/613121
DATED : January 8, 2013
INVENTOR(S) : Robert F. Wilson It is certified that error appears in the above-identified patent and that said Letters Patent is hereby corrected as shown below:

Column 6, line 28, "support" should read --device--.

Signed and Sealed this
Second Day of April, 2013

Teresa Stanek Rea
*Acting Director of the United States Patent and Trademark Office*